(12) United States Patent
Evans et al.

(10) Patent No.: US 9,474,865 B2
(45) Date of Patent: Oct. 25, 2016

(54) NEEDLE SHIELD FOR DISPOSABLE SYRINGE WITH ANNULAR RING

(71) Applicant: West Pharmaceutical Services, Inc., Exton, PA (US)

(72) Inventors: Christopher Evans, Long Valley, NJ (US); Brian Costello, Union, NJ (US); Christopher Gieda, Long Valley, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 210 days.

(21) Appl. No.: 13/870,330

(22) Filed: Apr. 25, 2013

(65) Prior Publication Data

US 2014/0323977 A1 Oct. 30, 2014

(51) Int. Cl.
*A61M 5/32* (2006.01)

(52) U.S. Cl.
CPC ......... *A61M 5/3243* (2013.01); *A61M 5/3257* (2013.01); *A61M 2005/3261* (2013.01)

(58) Field of Classification Search
CPC ........... A61M 5/3243; A61M 5/3257; A61M 2005/3261
USPC ....................... 604/192, 195, 198
See application file for complete search history.

(56) References Cited

U.S. PATENT DOCUMENTS

| | | | |
|---|---|---|---|
| 2,198,666 A | 4/1940 | Gruskin | |
| 2,701,566 A | 2/1955 | Krug | |
| 3,324,854 A | 6/1967 | Weese | |
| 3,459,177 A | 8/1969 | Deuschle | |
| 3,472,227 A | 10/1969 | Burke | |
| 3,523,531 A | 8/1970 | Burke | |
| 3,523,532 A | 8/1970 | Burke | |

(Continued)

FOREIGN PATENT DOCUMENTS

| | | | |
|---|---|---|---|
| CN | 1520320 A | 8/2004 |
| EP | 0216460 B1 | 9/1990 |

(Continued)

OTHER PUBLICATIONS

Office Action issued Apr. 8, 2014 in CN Application No. 201180013752.6.

(Continued)

*Primary Examiner* — Edelmira Bosques
(74) *Attorney, Agent, or Firm* — Panitch Schwarze Belisario & Nadel LLP

(57) ABSTRACT

A needle shield includes a body extending along a longitudinal axis, and having a longitudinal channel configured to receive a syringe. The body has injection and protection positions. A first latching mechanism on the body is radially outwardly deflectable and includes a protuberance extending radially into the channel. A second latching mechanism disposed on the body and proximally of the first latching mechanism is radially outwardly deflectable and includes a tab at a proximal end thereof extending radially into the channel. The tab has a radially inwardly tapering portion toward a proximal edge of the tab oriented generally perpendicularly with respect to the longitudinal axis. In the injection position, an annular ring on the syringe is located distally of the protuberance, and in the protection position, the proximal edge of the tab is in facing engagement with the annular ring to prevent proximal movement of the body on the syringe.

11 Claims, 3 Drawing Sheets

(56) References Cited

U.S. PATENT DOCUMENTS

| | | | |
|---|---|---|---|
| 3,556,099 A | 1/1971 | Knight et al. | |
| 3,756,235 A | 9/1973 | Burke et al. | |
| 3,903,887 A | 9/1975 | Antoshkiw | |
| 4,240,433 A | 12/1980 | Bordow | |
| 4,332,248 A | 6/1982 | DeVitis | |
| 4,393,870 A | 7/1983 | Wagner | |
| 4,568,346 A | 2/1986 | van Dijk | |
| 4,631,057 A | 12/1986 | Mitchell | |
| 4,737,144 A | 4/1988 | Choksi | |
| 4,747,837 A | 5/1988 | Hauck | |
| 4,795,445 A | 1/1989 | Jensen | |
| 4,801,295 A | 1/1989 | Spencer | |
| 4,850,996 A | 7/1989 | Cree | |
| 4,958,625 A | 9/1990 | Bates et al. | |
| 4,966,589 A | 10/1990 | Kaufman | |
| 4,998,920 A | 3/1991 | Johnson | |
| 5,053,018 A | 10/1991 | Talonn et al. | |
| 5,084,030 A | 1/1992 | Byrne et al. | |
| 5,108,378 A | 4/1992 | Firth et al. | |
| 5,197,953 A * | 3/1993 | Colonna | 604/110 |
| 5,282,793 A * | 2/1994 | Larson | 604/192 |
| 5,364,362 A | 11/1994 | Schulz | |
| 5,437,640 A | 8/1995 | Schwab | |
| 5,496,288 A | 3/1996 | Sweeney | |
| 5,520,653 A | 5/1996 | Reilly et al. | |
| 5,527,287 A | 6/1996 | Miskinyar | |
| 5,669,888 A | 9/1997 | Trapp | |
| 5,855,839 A | 1/1999 | Brunel | |
| 5,893,845 A | 4/1999 | Newby et al. | |
| 6,117,108 A | 9/2000 | Woehr et al. | |
| 6,200,291 B1 | 3/2001 | Di Pietro | |
| 6,494,865 B1 | 12/2002 | Alchas | |
| 6,569,123 B2 | 5/2003 | Alchas et al. | |
| 6,607,509 B2 | 8/2003 | Bobroff et al. | |
| 6,666,844 B1 | 12/2003 | Igo et al. | |
| 6,689,118 B2 | 2/2004 | Alchas et al. | |
| 6,776,776 B2 | 8/2004 | Alchas et al. | |
| 6,921,384 B2 | 7/2005 | Reilly et al. | |
| 6,939,322 B2 | 9/2005 | Crank et al. | |
| 7,052,483 B2 | 5/2006 | Wojcik | |
| 7,938,808 B2 * | 5/2011 | Pessin | 604/192 |
| 8,083,715 B2 | 12/2011 | Sonoda et al. | |
| 8,556,861 B2 | 10/2013 | Tsals | |
| 2001/0056265 A1 | 12/2001 | Heinz et al. | |
| 2002/0077599 A1 | 6/2002 | Wojcik | |
| 2002/0193744 A1 | 12/2002 | Alesi et al. | |
| 2003/0050602 A1 | 3/2003 | Pettis et al. | |
| 2003/0093032 A1 | 5/2003 | Py et al. | |
| 2003/0199822 A1 | 10/2003 | Alchas et al. | |
| 2004/0010234 A1 * | 1/2004 | Hung et al. | 604/198 |
| 2004/0147901 A1 | 7/2004 | Py et al. | |
| 2006/0079920 A1 | 4/2006 | Schraga | |
| 2007/0118077 A1 | 5/2007 | Clarke et al. | |
| 2007/0250016 A1 | 10/2007 | Pech et al. | |
| 2008/0154205 A1 | 6/2008 | Wojcik | |
| 2010/0137831 A1 | 6/2010 | Tsals | |
| 2011/0077602 A1 | 3/2011 | Yokota et al. | |
| 2011/0224609 A1 | 9/2011 | Tsals et al. | |

FOREIGN PATENT DOCUMENTS

| | | |
|---|---|---|
| EP | 0457477 A1 | 11/1991 |
| EP | 0702973 A2 | 3/1996 |
| EP | 2139543 A1 | 1/2010 |
| FR | 2612401 A1 | 9/1988 |
| FR | 2616331 A1 | 12/1988 |
| FR | 2616665 A2 | 12/1988 |
| JP | 02-046861 A | 2/1990 |
| JP | 08-107933 A | 4/1996 |
| JP | H11-512016 A | 10/1999 |
| JP | 2005-021247 A | 1/2005 |
| JP | 2010524646 T | 7/2010 |
| WO | 9507722 A1 | 3/1995 |
| WO | 9526764 A1 | 10/1995 |
| WO | 9709077 A1 | 3/1997 |
| WO | 9741907 A2 | 11/1997 |
| WO | 02083216 A1 | 10/2002 |
| WO | 2004071560 A1 | 8/2004 |
| WO | 2006052737 A1 | 5/2006 |
| WO | 2007026164 A2 | 3/2007 |
| WO | 2008131440 A1 | 10/2008 |
| WO | 2010064211 A2 | 6/2010 |
| WO | 2010077596 A1 | 7/2010 |
| WO | 2010087524 A2 | 8/2010 |
| WO | 2011011697 A1 | 1/2011 |
| WO | 2011112916 A1 | 9/2011 |

OTHER PUBLICATIONS

Office Action issued Apr. 11, 2014 in U.S. Appl. No. 13/386,099 by Tsals.
English translation of an Office Action issued Apr. 11, 2014 in CN Application No. 201080041235.5.
Office Action issued May 5, 2014 in CN Application No. 200980148920.5.
International Search Report Issued Mar. 29, 2010 in Int'l Application No. PCT/US2009/066960.
Int'l Search Report issued Oct. 27, 2010 in Int'l Application No. PCT/US2010/043071; Written Opinion.
Int'l Search Report issued on Sep. 16, 2008 in Int'l Application No. PCT/US08/61331; Written Opinion.
Int'l Preliminary Report on Patentability Issued Aug. 14, 2009 in Int'l Application No. PCT/US08/61331.
Int'l Search Report issued on Mar. 23, 2006 in Int'l Application No. PCT/US05/39979.
Int'l Preliminary Report on Patentability Issued May 8, 2007 in Int'l Application No. PCT/US05/039979; Written Opinion.
U.S. Appl. No. 13/057,006 by Tsals, filed Feb. 1, 2011.
Int'l Preliminary Report on Patentability issued Jun. 14, 2011 in Int'l Application No. PCT/US2009/066960.
Office Action issued Mar. 2, 2012 in U.S. Appl. No. 12/597,103 by Tsals.
Int'l Preliminary Report on Patentability issued Apr. 9, 2012 in Int'l Application No. PCT/US10/43071.
Office Action issued May 15, 2012 in JP Application No. 2010-506461 (with English translation of relevant portions).
International Search Report Issued Aug. 4, 2011 in Int'l Application No. PCT/US2011/028072.
Office Action issued Aug. 10, 2012 in U.S. Appl. No. 12/597,103 by Tsals.
U.S. Appl. No. 13/583,096 by Tsals, filed Sep. 6, 2012.
Int'l Preliminary Report on Patentability issued Sep. 27, 2012 in Int'l Application No. PCT/US2011/028072.
Office Action issued Mar. 14, 2013 in U.S. Appl. No. 12/597,103 by Tsals.
Office Action issued Apr. 15, 2013 in U.S. Appl. No. 13/057,006 by Tsals.
Office Action issued Apr. 24, 2013 in U.S. Appl. No. 13/583,096 by Tsals.
Office Action issued Apr. 30, 2013 in JP Application No. 2012-521832.
Int'l Search Report and Written Opinion issued May 27, 2014 in Int'l Application No. PCT/US2014/019907.
Office Action issued Aug. 2, 2013 in U.S. Appl. No. 13/057,006 by Tsals.
Office Action issued Jul. 7, 2014 in CN Application No. 200980148920.5.
Office Action issued Jan. 14, 2014 in U.S. Appl. No. 13/355,031 by Tsals.
Extended European Search Report issued Sep. 8, 2014 in EP Application No. 08746707.2.
Office Action issued Dec. 31, 2014 in U.S. Appl. No. 13/583,096 by Tsals.
Office Action issued Nov. 26, 2013 in JP Application No. 2012-521832.
Office Action issued Jan. 6, 2014 in U.S. Appl. No. 13/057,006 by Tsals.

(56) References Cited

OTHER PUBLICATIONS

Office Action issued Dec. 17, 2013 in EP Application No. 11 710 607.0.
Office Action issued Jun. 13, 2013 in CN Application No. 201080041235.5.
Office Action issued Nov. 22, 2013 in U.S. Appl. No. 13/583,096 by Tsals.
English translation of an Office Action issued Sep. 29, 2014 in CN Application No. 201080041235.5.
Office Action issued Nov. 6, 2014 in U.S. Appl. No. 13/386,099 by Tsals.
Office Action issued Apr. 28, 2015 in U.S. Appl. No. 13/583,096 by Tsals.
Office Action issued Sep. 10, 2015 in U.S. Appl. No. 13/583,096 by Tsals.
Int'l Preliminary Report on Patentability issued Sep. 17, 2015 in Int'l Application No. PCT/US2014/019907.
Office Action issued Dec. 16, 2015 in EP Application No. 087467072.

\* cited by examiner

NEEDLE SHIELD FOR DISPOSABLE SYRINGE WITH ANNULAR RING

BACKGROUND OF THE INVENTION

Embodiments of the present invention relate generally to needle safety systems, and more particularly, to a needle shield for use with a syringe having an annular ring formed on the barrel thereof.

Safety devices for preventing accidental needle sticks to patients, doctors, medical personnel, and the like are known. Such devices typically include some form of sheath or shield that is actuated to cover the end of the needle before and/or following injection. Such devices often involve multiple parts for attachment to the syringe and complex actuation mechanisms. These conventional designs increase cost, the likelihood of failure of the device, and the likelihood of confusion by the user.

It is desirable to provide a single component, easy-to-use needle shield that can utilize existing features of a syringe for enabling protection of the sharp end of the needle.

BRIEF SUMMARY OF THE INVENTION

Briefly stated, a preferred embodiment of the present invention comprises a needle shield for a syringe having a barrel, a needle having a sharp end arranged at a distal end of the barrel, and a generally annular ring proximate the distal end of the barrel and extending radially outwardly from the barrel. The needle shield includes a body extending between a distal end and a proximal end along a longitudinal axis. The body has a longitudinal channel formed therein and is configured to receive the syringe such that the body partially surrounds the barrel of the syringe. The body is movable between a first position on the syringe wherein the sharp end of the needle extends distally beyond the distal end of the body and a second position on the syringe wherein the distal end of the body extends distally beyond the sharp end of the needle. A longitudinal opening is formed in the body and accesses the longitudinal channel. A first latching mechanism is disposed longitudinally along the body proximate a distal end of the body. The first latching mechanism is radially outwardly deflectable and includes a protuberance at a distal end thereof that extends radially into the longitudinal channel when the first latching mechanism is in a rest position. A second latching mechanism is disposed longitudinally along the body and proximally with respect to the first latching mechanism. The second latching mechanism is radially outwardly deflectable and includes a tab at a proximal end thereof that extends radially into the longitudinal channel when the second latching mechanism is in a rest position. The tab has a radially inwardly tapering portion toward a proximal edge of the tab oriented generally perpendicularly with respect to the longitudinal axis. When the body is in the first position, the annular ring on the barrel of the syringe is located distally of the protuberance of the first latching mechanism, and when the body is in the second position, the proximal edge of the tab of the second latching mechanism is in facing engagement with the annular ring on the barrel of the syringe to prevent proximal movement of the body relative to the syringe.

Another preferred embodiment of the present invention comprises a needle safety system including a syringe having a barrel, a needle having a sharp end arranged at a distal end of the barrel, and a generally annular ring proximate the distal end of the barrel and extending radially outwardly from the barrel. A needle shield includes a body extending between a distal end and a proximal end along a longitudinal axis. The body has a longitudinal channel formed therein and is configured to receive the syringe such that the body partially surrounds the barrel of the syringe. The body and the syringe are movable with respect to each other between a first position wherein the sharp end of the needle extends distally beyond the distal end of the body and a second position wherein the distal end of the body extends distally beyond the sharp end of the needle. A longitudinal opening is formed in the body and accesses the longitudinal channel. A first latching mechanism is disposed longitudinally along the body proximate a distal end of the body. The first latching mechanism is radially outwardly deflectable and includes a protuberance at a distal end thereof that extends radially into the longitudinal channel when the first latching mechanism is in a rest position. A second latching mechanism is disposed longitudinally along the body and proximally with respect to the first latching mechanism. The second latching mechanism is radially outwardly deflectable and includes a tab at a proximal end thereof that extends radially into the longitudinal channel when the second latching mechanism is in a rest position. The tab has a radially inwardly tapering portion toward a proximal edge of the tab oriented generally perpendicularly with respect to the longitudinal axis. During movement of the syringe and needle shield from the first position to the second position the annular ring of the syringe is configured to (i) contact the protuberance and outwardly deflect the first latching mechanism to allow the annular ring to pass the protuberance in a proximal direction, and (ii) contact the tab and outwardly deflect the second latching mechanism to allow the annular ring to pass the tab in a proximal direction such that after the annular ring passes the tab and the second latching mechanism returns to the rest position, the proximal edge of the tab is in facing engagement with the annular ring and prevents proximal movement of the body relative to the syringe.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
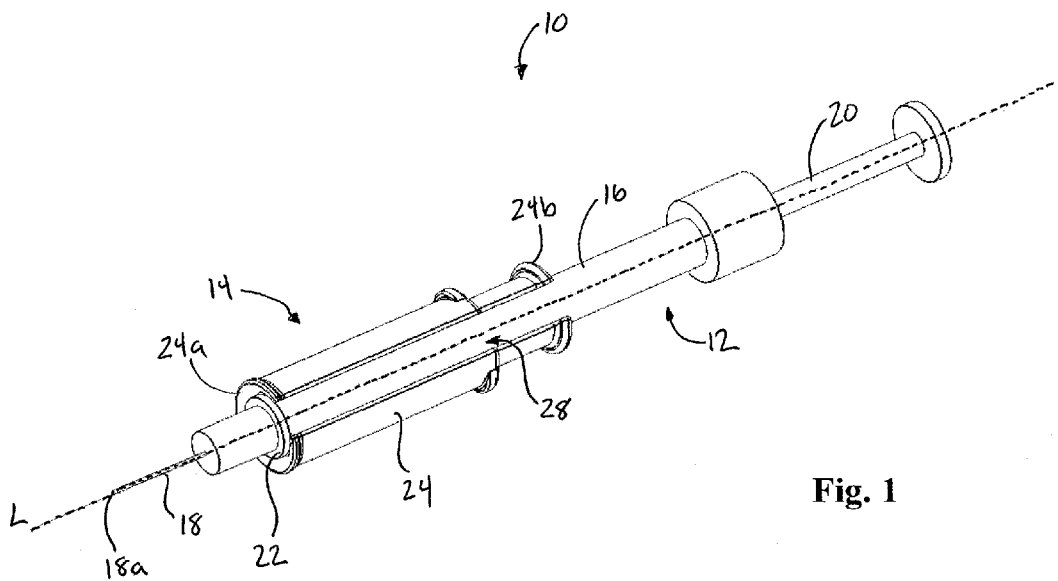
FIG. 1 is a front-side perspective view of a syringe and needle shield in an injection position in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the needle safety system and designated parts thereof. Unless specifically set forth herein, the terms "a", "an" and "the" are not limited to one element but instead should be read as meaning "at least one". The terminology includes the words noted above, derivatives thereof and words of similar import.

Figure 2:
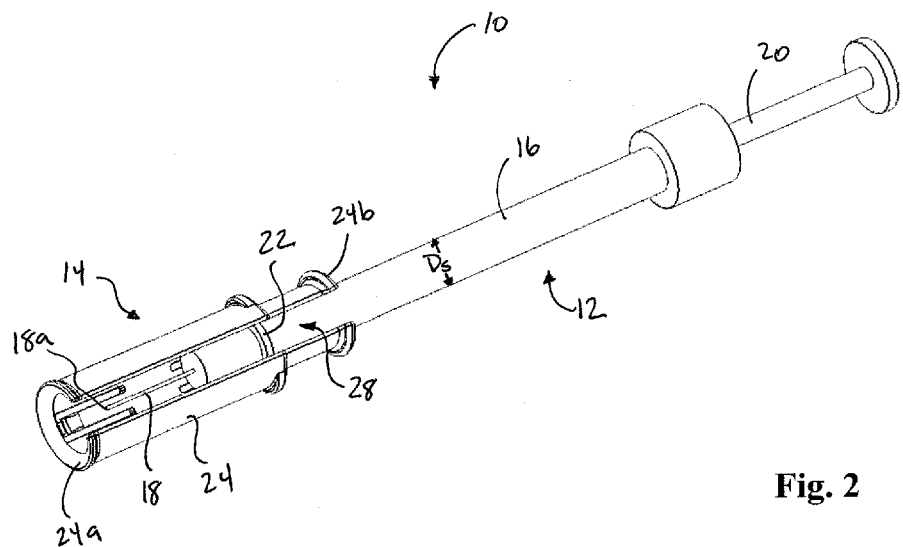
FIG. 2 is a front-side perspective view of the syringe and needle shield of FIG. 1 in a protection position.

Referring to the drawings, wherein the same reference numerals are used to designate the same components throughout the several figures, there is shown in FIGS. 1 and 2 a needle safety system 10 in accordance with a preferred embodiment of the present invention. The system 10 includes a syringe 12 and a needle shield 14. The syringe 12 is preferably conventional and includes a barrel 16 for containing medicament (not shown) to be administered to a patient. A needle 18 is arranged at a distal end of the barrel 16 and in fluid communication therewith for transmission of the medicament. The needle 18 includes a sharp distal end 18a which the needle shield 14 is intended to cover post-injection. The syringe 12 also preferably includes a plunger 20 that is movably received within the barrel 16 through a proximal end of the barrel 16 opposite to the needle 18.

The syringe 12 also preferably includes a generally annular ring 22 located proximate the distal end of the barrel 16 and extending radially outwardly therefrom. The annular ring 22 preferably entirely encircles the barrel 16, but may have one or more breaks (not shown) formed therein. Additionally, the annular ring 22 need not be circular in form, and may instead be eccentric, square, rectangular, or the like. It is preferred that the annular ring 22 is integrally formed with the barrel 16 of the syringe 12, although it is also contemplated that the annular ring 22 may be fixedly attached to the barrel 16, such as by welding, adhesives, mechanical fasteners, or the like, or may be removably attachable to the barrel 16, such as by a mechanical fastener, friction-fit, or the like.

The needle shield 14 includes a body 24 that extends between a distal end 24a and a proximal end 24b along a longitudinal axis L. The body 24 is preferably made from a molded polymeric material and includes a longitudinal channel 26 (FIG. 5) formed therein that is configured to receive the syringe 12 such that the body 24 at least partially surrounds and engages the barrel 16 of the syringe 12. The body 24 of the needle shield 14 is slidable along the barrel 16 of the syringe 12 between an injection position (FIG. 1), wherein the sharp end 18a of the needle 18 of the syringe 12 is exposed and extends distally beyond the distal end 24a of the body 24, and a protection position (FIG. 2), wherein the distal end 24a of the body 24 extends distally beyond the sharp end 18a of the needle 18 such that the sharp end 18a of the needle 18 is covered and the user is protected from an accidental needle stick.

In a preferred embodiment, the body 24 also has a longitudinal opening 28 formed therein that extends the length of the body 24 generally parallel with the longitudinal axis L. The longitudinal opening 28 accesses the longitudinal channel 26 and permits insertion of the syringe 12 into the needle shield 14. The longitudinal opening 28 specifically permits a medical professional to engage the syringe 12 with the needle shield 14 prior to injection of the medicament into the patient. Typically, the needle shield 14 is packaged in a sterile package and removed from the package for assembly with the syringe 12 prior to injecting the medicament into the patient. Accordingly, a plurality of packaged needle shields 14 and a plurality of syringes 12 can be stored at an injection site and assembled when necessary prior to injecting medicament into patients.

Figure 3:
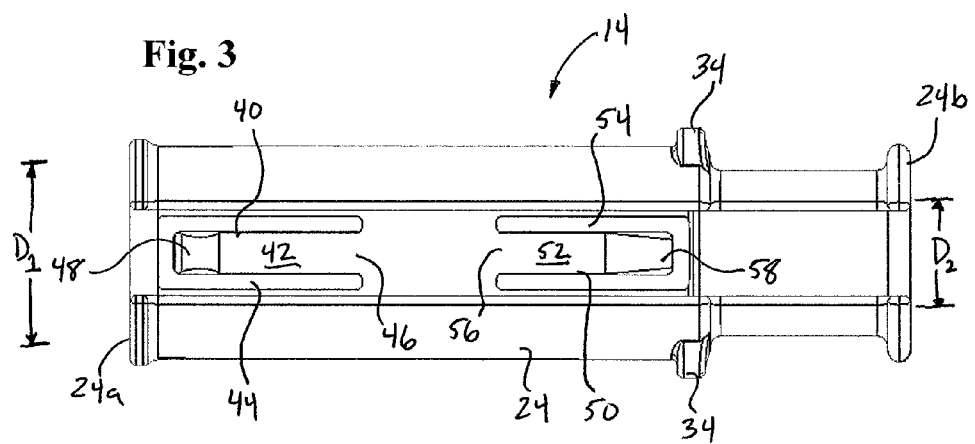
FIG. 3 is a front-side elevational view of the needle shield of FIG. 1.
Figure 4:
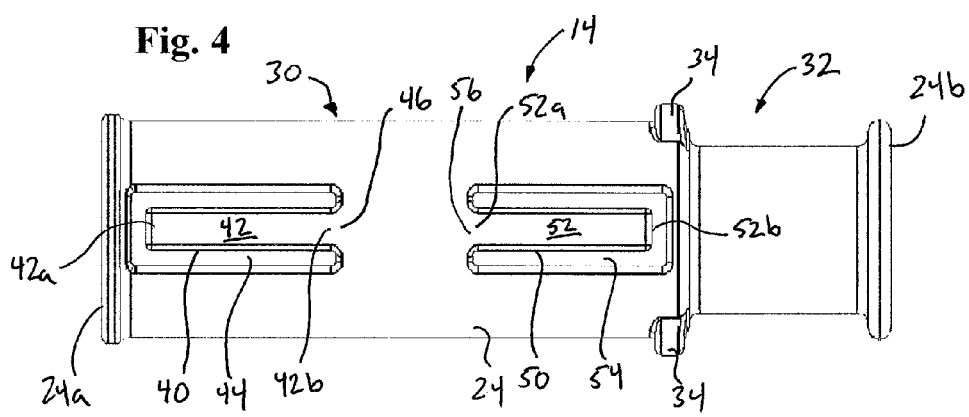
FIG. 4 is a back-side elevational view of the needle shield of FIG. 1.
Figure 5:
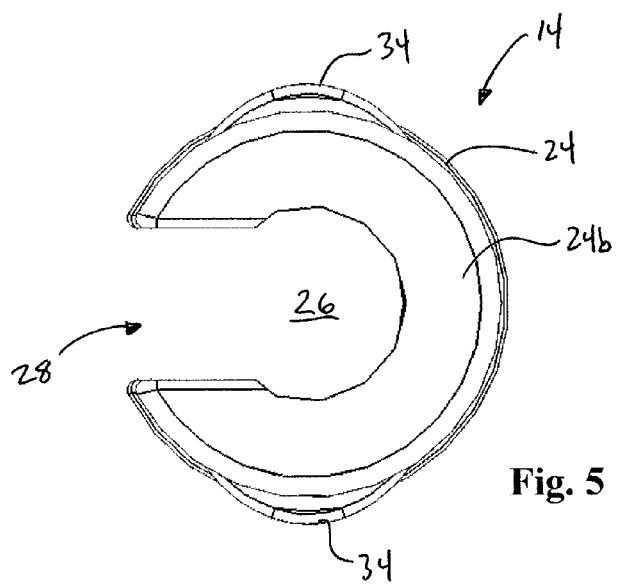
FIG. 5 is a right-side elevational view of the needle shield of FIG. 1.
Figure 6:
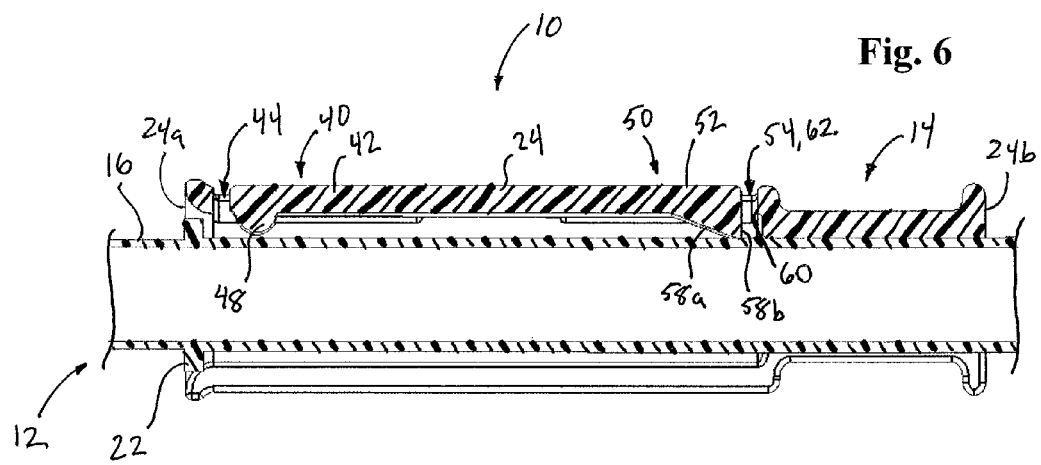
FIG. 6 is an enlarged partial front-side cross-sectional view of the syringe and needle shield of FIG. 1.

Referring to FIGS. 3-5, it is preferred that the needle shield body 24 includes at least two distinct portions, such as a first portion 30 proximate the distal end 24a of the body 24 and a second portion 32 proximate the proximal end 24b of the body. An outer surface of the second portion 32, for example, preferably forms a user-gripping portion that is sufficiently distanced from the sharp end 18a of the needle 18 to allow the user to move the needle shield 14 along the barrel 16 of the syringe 12 between the injection and protection positions. For example, the outer surface of the second body portion 32 may be roughened, knurled, have a raised pattern, or the like to enable the user to maintain a tight grip on the body 24. In addition, at least one, and preferably a pair of diametrically opposed flanges 34 are provided, preferably between the first and second body portions 24a, 24b. The flanges 34 are engageable with fingers of the user to permit the user to provide additional force to move the needle shield 14 along the barrel 16 of the syringe 12. The flanges 34 are shown extending radially outwardly from an outer surface of the first body portion 30, although the flanges 34 may also or alternatively extend radially outwardly from the outer surface of the second body portion 32.

It is further preferred that the longitudinal channel 26 have differing cross-sectional diameters $D_1$, $D_2$ in the first and second body portions 30, 32. For example, the longitudinal channel 26 in the second body portion 32 preferably has a diameter $D_2$ that is at least slightly greater than or closely approximates a diameter $D_S$ (FIG. 2) of the barrel 16 of the syringe 12. The second body portion 32 thereby creates a frictional engagement of the needle shield 14 with the syringe 12. Alternatively or additionally, the longitudinal channel 26 within the second body portion 32 may have a polygonal shape in cross-section (FIG. 5) to further aid in firm engagement of the needle shield 14 with the syringe 12. The longitudinal channel 26 in the first body portion 30 preferably has a larger diameter $D_1$ than in the second body portion 32, and is at least slightly greater than the outer diameter of the annular ring 22 on the barrel 16 of the syringe 12.

The above-described configuration of the needle shield body 24 is only preferred, and other configurations are possible. For example, the longitudinal channel 26 may have a constant diameter throughout the body 24 except at the proximal end 24b of the body, or the longitudinal channel 26 may include a number of different diameters. In addition, despite differing internal diameters, the outer surface of the body 24 may nonetheless have a generally constant outer diameter.

Referring to FIGS. 3, 4, 6, and 7, the needle shield 14 further includes a first latching mechanism 40 that is disposed longitudinally along the body 24 (preferably aligned with the longitudinal axis L) proximate the distal end 24a thereof. The first latching mechanism 40 is preferably in the form of an elongated arm 42 having a free distal end 42a and a proximal end 42b that is coupled to the body 24 such that the distal end 42a of the arm 42 is radially outwardly deflectable. The body 24 preferably includes a generally U-shaped first aperture 44 within which the arm 42 is disposed to allow movement thereof. The arm 42 is preferably formed with the needle shield body 24 or may be coupled to the body 24 by a living hinge 46, although other methods of attachment, such as welding, adhesives, mechanical fasteners, or the like, may be used as well.

The first latching mechanism 40 preferably also includes a protuberance 48 located on the inner surface of the distal end 42a of the arm 42. When the arm 42 is in a rest position (i.e., the state shown in the drawings wherein no forces are applied to deflect the arm 42), the protuberance 48 extends radially into the longitudinal channel 26. The protuberance 48 is preferably rounded, at least along the longitudinal axis L, although the protuberance 48 may take the form of tapered portions or the like. In this way, a structure such as the annular ring 22 of the syringe 12 is inhibited from passing the protuberance 48 in either the distal or proximal direction absent a sufficient amount of force applied by the user. This configuration generally prevents accidental activation of the needle shield 14 but allows return of the needle shield 14 to the injection position in the event of an accidental trigger.

The needle shield 14 further includes a second latching mechanism 50 that is disposed longitudinally along the body 24 (preferably aligned with the longitudinal axis L) proximally from the first latching mechanism 40. It is preferred that the second latching mechanism 50 be provided within the first body portion 30 at least slightly distal from the flanges 34 to avoid interference with the second latching mechanism 50 by the grip of the user. Similar to the first latching mechanism 40, the second latching mechanism 50 is preferably in the form of an elongated arm 52 having a distal end 52a that is coupled to the body 24 and a free proximal end 52b, and is radially outwardly deflectable. The body 24 preferably includes a generally U-shaped second aperture 54 within which the proximal end 52b of the arm 52 is disposed to allow movement thereof. The arm 52 is preferably formed with the needle shield body 24 or may be coupled to the body 24 by a living hinge 56, although other methods of attachment, such as welding, adhesives, mechanical fasteners, or the like, may be used as well.

The second latching mechanism 50 preferably also includes a tab 58 located on the inner surface of the proximal end 52b of the arm 52. When the arm 52 is in a rest position (similar to the first latching mechanism 40), the tab 58 extends radially into the longitudinal channel 26. The tab 58 has a ramped portion 58a that preferably tapers radially inwardly toward a proximal edge 58b of the tab 58, which is preferably oriented generally perpendicularly with respect to the longitudinal axis L. The proximal edge 58b of the tab 58 is configured to prevent proximal movement of the body 24 with respect to the syringe 12 by facially engaging the annular ring 22 of the syringe 12 when the needle shield 14 is in the protection position (see FIG. 7).

Figure 7:
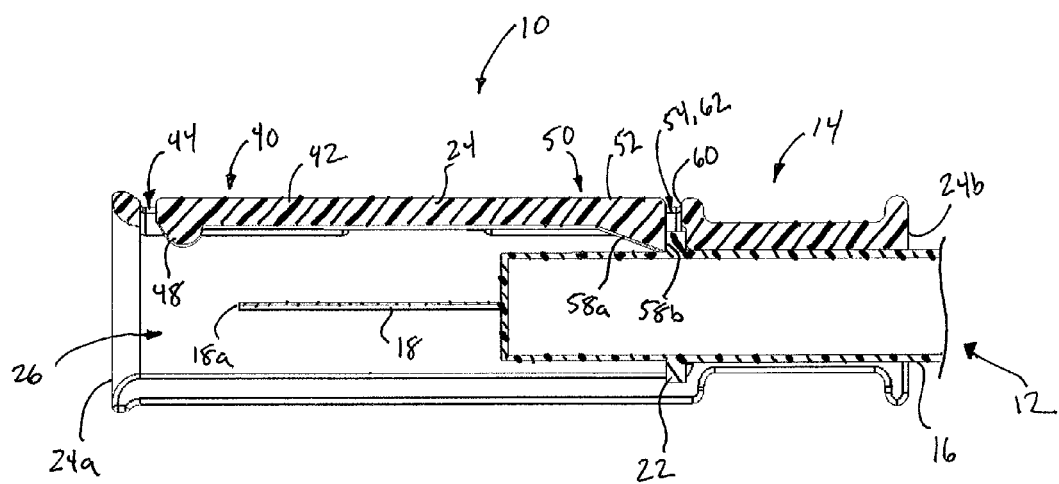
FIG. 7 is an enlarged partial front-side cross-sectional view of the syringe and needle shield in the protection position of FIG. 2.

It is further preferred that a distal end of the second body portion 32, such as the location of transition between the diameters $D_1$, $D_2$, forms a distal edge 60 that faces the proximal edge 58b of the tab 58, thereby forming a slot 62 configured to receive the annular ring 22 of the syringe 12 when the needle shield 14 is in the protection position (see FIG. 7). The proximal edge 58b of the tab 58 and the distal edge 60 prevent movement of the needle shield 14 relative to the syringe 12 in either direction along the longitudinal axis L when in the protection position.

Operation of the needle safety system 10 will now be described. The syringe 12 is mounted to the needle shield 14, preferably by press-fitting the syringe 12 through the longitudinal opening 28 of the body 24 and into the longitudinal channel 26. Mounting of the needle shield 14 on the syringe 12 typically occurs before or after aspiration of medicament into the syringe 12 (if necessary), but preferably before injection into the patient. However, it is contemplated that the needle shield 14 may be mounted to the syringe 12 after the injection has taken place. In the assembled configuration in the injection position (e.g., FIGS. 1, 6), the annular ring 22 on the barrel 16 of the syringe 12 is located distally of the protuberance 48 of the first latching mechanism 40 and the sharp end 18a of the needle 18 is exposed.

Once the injection has taken place by moving the plunger 20 within the barrel 16 to expel the medicament through the needle 18, the user may grasp the second body portion 32 (or any other gripping portion of the body 24) with one hand and use the other hand to grasp the barrel 16 of the syringe 12. With sufficient force, the annular ring 22 is brought into contact with the protuberance 58 by moving the syringe 12 in a proximal direction with respect to the needle shield 14. The force of the annular ring 22 against the protuberance deflects the arm 42 of the first latching mechanism 40 radially outwardly, allowing the annular ring 22 to pass the protuberance in the proximal direction.

Once the annular ring 22 has passed the protuberance and the arm 42 of the first latching mechanism 40 has returned to its rest position, the user continues to move the syringe 12 in the proximal direction with respect to the needle shield 14. Eventually, the annular ring 22 is brought into contact with the ramped portion 58a of the tab 58 of the second latching mechanism 50. The force of the annular ring 22 against the tab 58 deflects the arm 52 of the second latching mechanism 52 radially outwardly, allowing the annular ring to pass the tab 58 in the proximal direction. Once the annular ring 22 has passed the tab 58, the arm 52 of the second latching mechanism 50 returns to its rest position, and the annular ring 22 enters the slot 62 and is in facing engagement with the proximal edge 58b of the tab 58, thereby preventing proximal movement of the needle shield 14 with respect to the syringe 12. Preferably the distal edge 60 of the second body portion 32 is also in facing engagement with the annular ring 22 and prevents distal movement of the needle shield 14 with respect to the syringe 12. The needle shield 14 is therefore locked in the protection position (FIGS. 2, 7) and the sharp end 18a of the needle 18 is safely contained within the longitudinal channel 26 in the body 24 of the needle shield 14.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:
1. A needle safety system comprising:
a syringe having a barrel, a needle having a sharp end arranged at a distal end of the barrel, and a generally annular ring proximate the distal end of the barrel and extending radially outwardly from the barrel; and
a needle shield comprising:
a body extending between a distal end and a proximal end along a longitudinal axis, the body having a longitudinal channel formed therein and being configured to receive the syringe such that the body partially surrounds the barrel of the syringe, the body and the syringe being movable with respect to each other between a first position wherein the sharp end of the needle extends distally beyond the distal end of the body and a second position wherein the distal end of the body extends distally beyond the sharp end of the needle;

a longitudinal opening formed in the body and extending from the distal end to the proximal end of the body, the longitudinal opening accessing the longitudinal channel;

a first latching mechanism disposed longitudinally along the body proximate a distal end of the body, the first latching mechanism being radially outwardly deflectable and including a protuberance at a distal end thereof that extends radially into the longitudinal channel when the first latching mechanism is in a first rest position; and a second latching mechanism disposed longitudinally along the body and proximally with respect to the first latching mechanism, the second latching mechanism being radially outwardly deflectable and including a tab at a proximal end thereof that extends radially into the longitudinal channel when the second latching mechanism is in a second rest position, the tab having a radially inwardly tapering portion toward a proximal edge of the tab oriented generally perpendicularly with respect to the longitudinal axis, wherein during movement of the syringe and needle shield from the first position to the second position the annular ring of the syringe is configured to:

(i) contact the protuberance and outwardly deflect the first latching mechanism to allow the annular ring to pass the protuberance in a proximal direction, and (ii) contact the tab and outwardly deflect the second latching mechanism to allow the annular ring to pass the tab in a proximal direction such that after the annular ring passes the tab and the second latching mechanism returns to the second rest position, the proximal edge of the tab is in facing engagement with the annular ring and prevents proximal movement of the body relative to the syringe.

2. The needle safety system of claim 1, wherein one or both of the first and second latching mechanisms are coupled to the body by a living hinge.

3. The needle safety system of claim 1, wherein the first and second latching mechanisms are aligned along the longitudinal axis.

4. The needle safety system of claim 1, wherein the annular ring is one of integrally formed with the barrel of the syringe, fixedly attached to the barrel of the syringe, or removably attachable to the barrel of the syringe.

5. The needle safety system of claim 1, wherein the body includes a first portion proximate the distal end of the body and a second portion proximate the proximal end of the body, the longitudinal channel having a first inner diameter in the first portion of the body and a second inner diameter in the second portion of the body.

6. The needle safety system of claim 5, wherein a distal end of the second portion forms a distal edge, at least a portion of which faces the proximal edge of the tab of the second latching mechanism.

7. The needle safety system of claim 6, wherein the distal edge of the second body portion and the proximal edge of the tab of the second latching mechanism form a slot configured to receive the annular ring when the syringe and the needle shield are in the second position.

8. The needle safety system of claim 5, wherein an outer surface of the second body portion comprises a user-gripping portion.

9. The needle safety system of claim 8, wherein the body includes at least one flange extending radially outwardly from the body proximate a distal end of the second body portion.

10. The needle safety system of claim 5, wherein the first diameter is generally equal to a diameter of the annular flange and the second diameter is generally equal to a diameter of the barrel of the syringe.

11. The needle safety system of claim 5, wherein the longitudinal channel within the second body portion has a polygonal shape in cross-section.

* * * * *